US007254566B2

(12) United States Patent
Merkle

(10) Patent No.: US 7,254,566 B2
(45) Date of Patent: Aug. 7, 2007

(54) SYSTEM AND METHOD FOR MEDICAL DIAGNOSIS

(76) Inventor: Van D. Merkle, 5661 Willow Twig La., Centerville, OH (US) 45459

( * ) Notice: Subject to any disclaimer, the term of this patent is extended or adjusted under 35 U.S.C. 154(b) by 462 days.

(21) Appl. No.: 10/743,582

(22) Filed: Dec. 22, 2003

(65) Prior Publication Data

US 2005/0137463 A1 Jun. 23, 2005

(51) Int. Cl.
*G06N 5/00* (2006.01)
*A61B 5/00* (2006.01)

(52) U.S. Cl. .......................... 706/45; 600/300
(58) Field of Classification Search ............... 706/45; 600/300
See application file for complete search history.

(56) References Cited

U.S. PATENT DOCUMENTS

| | | | |
|---|---|---|---|
| 4,290,114 A | 9/1981 | Sinay | |
| 4,733,354 A | 3/1988 | Potter et al. | |
| 5,255,187 A | 10/1993 | Sorensen | |
| 5,404,292 A | 4/1995 | Hendrickson | |
| 5,551,436 A | 9/1996 | Yago | |
| 5,594,637 A | 1/1997 | Eisenberg et al. | |
| 5,660,176 A | 8/1997 | Iliff | |
| 5,746,204 A | 5/1998 | Schauss | |
| 5,993,386 A | 11/1999 | Ericsson | |
| 6,021,404 A | 2/2000 | Moukheibir | |
| 6,063,026 A | 5/2000 | Schauss et al. | |
| 6,149,585 A | 11/2000 | Gray | |
| 6,267,722 B1 * | 7/2001 | Anderson et al. ........... 600/300 |
| 6,270,456 B1 | 8/2001 | Iliff | |
| 6,273,854 B1 | 8/2001 | Kane et al. | |
| 6,277,070 B1 | 8/2001 | Kane et al. | |
| 6,394,952 B1 | 5/2002 | Anderson et al. | |
| 6,475,143 B2 | 11/2002 | Iliff | |

OTHER PUBLICATIONS

I. Hatzilygeroudis et al., XBONE: A Hybrid Expert System Supporting Diagnosis of Bone Diseases, 1997, Published in the Proceedings of the Medical Informatics Europe'97 (MIE'97).*
I. Hatzilygeroudis et al.(2), An Intelligent Medical System for Diagnosis of Bone Diseases, 1994, Published in the Proceedings of the 1st International Conference on Medical Physics and Biomedical Engineering (MPBE'94), vol. I, 148-152.*

* cited by examiner

*Primary Examiner*—Anthony Knight
*Assistant Examiner*—Nathan H. Brown, Jr.
(74) *Attorney, Agent, or Firm*—Thompson Hine LLP

(57) ABSTRACT

A system and method for generating a medical diagnosis is provided. In a first embodiment of the present invention a conversion table is created and stored in a computerized storage media of a computerized system, the conversion table converts raw test data into numeric values. Furthermore, a sub-diagnosis database is created and stored in the storage media, the sub-diagnosis database including a plurality of rules, each rule being identified by at least one diagnosis parameter. Patient test results are then input to the computerized system where they are converted into numeric analyte values by the conversion table. The numeric analyte values are compared to the diagnosis parameters of the rules stored in the sub-diagnosis database, wherein the rules having diagnosis parameters corresponding to the numeric analyte values are saved in the computerized system.

28 Claims, 7 Drawing Sheets

SYSTEM AND METHOD FOR MEDICAL DIAGNOSIS

BACKGROUND

The present invention relates to computerized medical diagnostic techniques, and more particularly, to computerized systems and methods for performing medical diagnoses that take into account various combinations of patient test results and other data.

The last 100 years have produced a tremendous volume of knowledge of the human body, its disease processes and the treatment of many disease processes using alternative natural care, including dietary modification and vitamin and nutrient supplementation. It is not possible for any individual practitioner to remember all of the analyte levels and the relationships and variables of the different tests as well as interpret the meaning of all of the relationships and variables of the different tests that are available with current medical testing technology.

Accordingly, computerized medical diagnostic systems and methods have been developed. Such systems receive medical test results of a patient and generate a diagnosis based on those test results. One such system is disclosed in U.S. Pat. No. 6,277,070 which is directed to a computerized diagnostic system in which a patient is given medical tests and the test results ("analytes") are then put into a computer system to assess whether the patient's analyte levels are low, high or average, compared to a typical group. The analyte levels are then compared with vitamin and nutrient data in a database to determine which vitamins and nutrients would have a positive or negative effect on the analyte. Those vitamins and nutrients having a positive effect on the analyte levels are retrieved from the database and reported. Treatment plans and other remedial measures may also be suggested. That diagnostic system provides the same result for each analyte value regardless of the presence of other varying analyte values from other tests.

A problem with such computerized diagnostic systems and methods is that they lack the ability to take into account the multiple inter-relationships of various test factors and the roles the combinations and inter-relationships of those factors and test results have on creating a proper and accurate diagnosis. Accordingly, there is a need for a computerized medical diagnostic system and method that is capable of generating a diagnosis and treatment regimen in which numerous test results are considered in combination.

SUMMARY

In light of the foregoing, the present invention is a computerized system and method for medical diagnosis that takes into account various combinations of patient test results and other data and generates a more specific and accurate diagnosis based on the inter-relationships of the test results and other data. The present invention provides a system and method for performing patient test analysis, test reporting and provides recommended treatment in response to multiple test results.

The system and method of the present invention include the use of a computer system for exploring several databases. The databases contain medical research and patient data regarding various analyte characteristics, the multiple inter-relationships that various analytes have on one another, as well as diagnoses and treatment regimens. The databases may be populated with live patient data or known medical statistics.

This invention utilizes medical tests that produce numeric results or tests whose results can be quantified. The primary analytes for testing include blood, hair, urine and saliva, among others. Within these primary analytes, the method and system may utilize more specific analytes. For example, the primary analyte blood may include two specific analytes: glucose level and iron level. The treating professional selects the analytes used for the diagnosis. The invention generates a medical diagnosis of high specificity based on the inter-relationships of the selected analyte test results.

This invention provides the practitioner and patient a comprehensive report with treatment and preventative recommendations, while improving productivity and saving time for the practitioner and staff. It will also improve accuracy, completeness, conformity to accepted protocols and compliance with the patient. Patients will be able to review their test results and report whenever they wish.

Other objects and advantages of the present invention will be apparent from the following description, the accompanying drawings and the appended claims.

BRIEF DESCRIPTION OF THE DRAWINGS

The invention could be understood with reference to the following drawings. In the drawings, like reference numerals designate corresponding parts throughout the several views.

DETAILED DESCRIPTION

Figure 1:
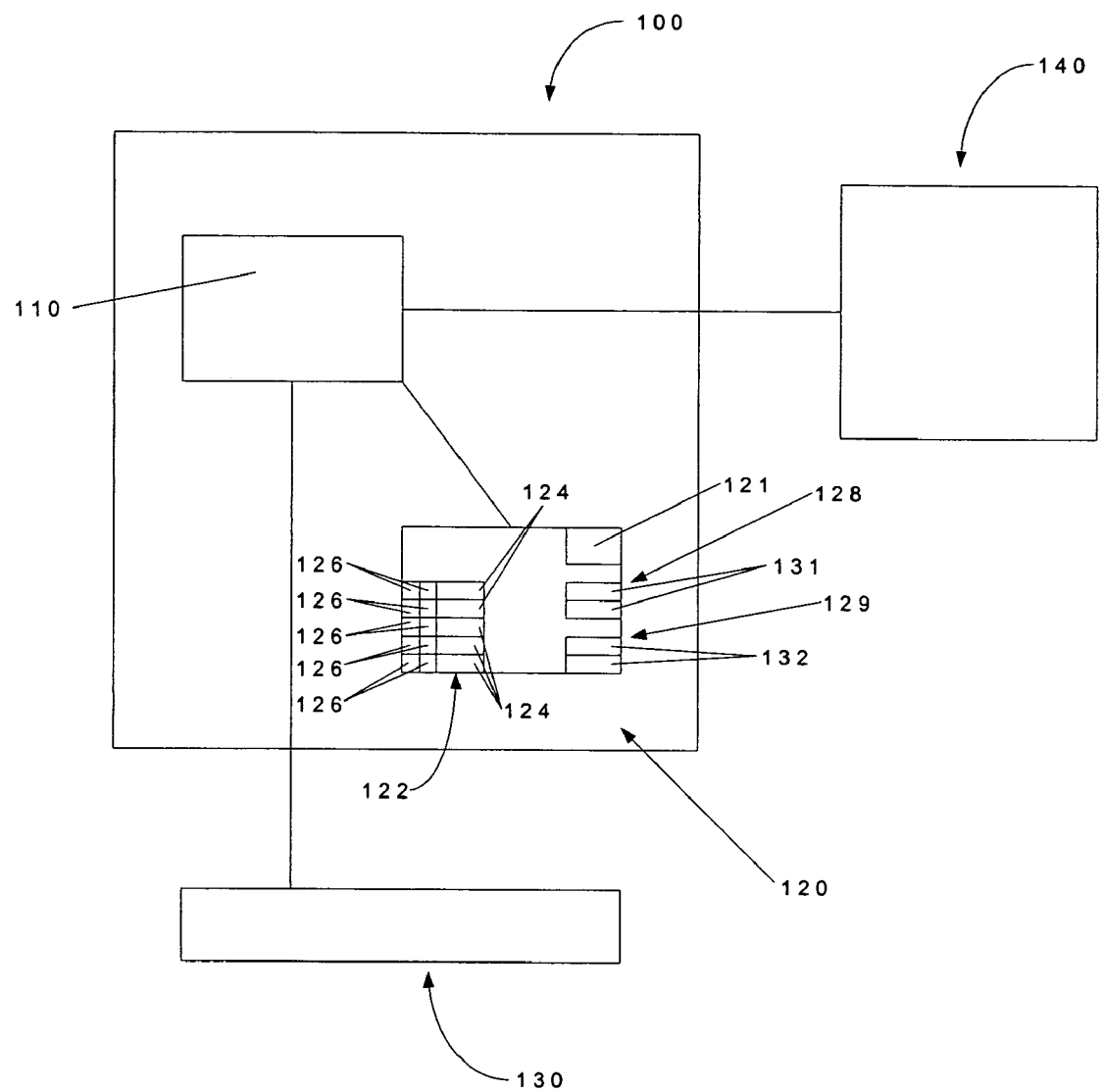
FIG. 1 is a block diagram illustrating the system of the present invention.

With reference to FIG. 1, the system of the present invention is embodied in a computer or computer network, generally designated 100 which is programmed with software to perform the process of the invention. The computerized system 100 may include a processor 110, storage media 120 and an input device 130, such as a keyboard, scanner or connection to a network, such as the Internet. The present invention may also include an output device 140 for displaying diagnostic results in a manner that is easy to view and comprehend. The output device 140 may be a monitor, printer, other like device or a combination thereof.

A conversion table 121 is created and stored in the storage media 120 of the computerized system 100. The conversion table 121 is a database populated with data obtained from live patient data and generally recognized medical information. The data stored in the conversion table 121 is used to convert medical test results and other patient information into numeric values. The process by which this is accomplished is referred to as the rating process 300 and is set forth in the discussion of FIG. 3 below.

A sub-diagnosis database 122 is created and stored in the storage media 120 of the computerized system 100 and is populated with a plurality of rules 124 that have been written to address at least the most common combinations of analytes. Each rule 124 is identified by at least one diagnosis parameter 126. The rules 124 making up the sub-diagnosis database 122 are derived from actual patient data. The rules 124 might also come from recognized medical information or any other pertinent sources. The process of matching relevant rules 124 to specific patient data is referred to as the searching process 400 and is set forth in the discussion of FIG. 4 below.

Figure 2:
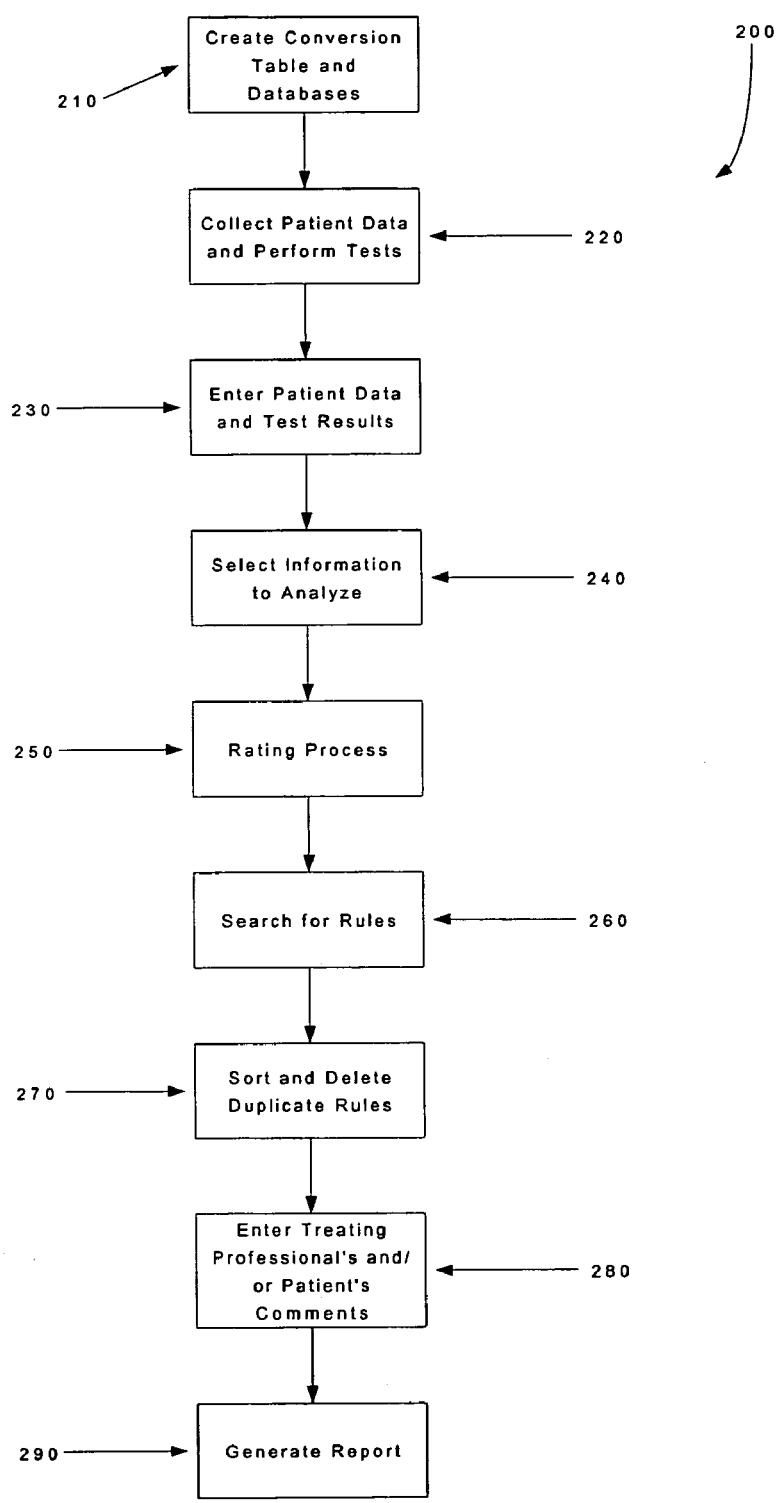
FIG. 2 is a flow chart illustrating the method of the present invention.

A first embodiment of the method 200 of the present invention involves the following steps, as shown in FIG. 2. As shown in block 210, the process begins with the storing of a conversion table 121 and sub-diagnosis database 122 in the storage media 120 of the computerized system 100. Next, as shown in block 220, the patient provides a treating professional with specific patient information, such as age, weight, height, current symptoms, and the like. Also as shown in block 220, based on the patient information provided, certain tests are then performed. As shown in block 230, the patient information and test results are retrieved and keyed into the computerized system 100 using the input device 130 or transferred to the present invention as a file. As shown in block 240, the treating professional then determines what information will be used to generate a diagnosis. Next, as shown in block 250, the system converts the patient information and test results into numeric analyte values using the conversion table 121 during the rating process 300. The numeric analyte values are then stored in the storage media 120. As shown in block 260, the system then searches the sub-diagnosis database 122 for all rules 124 that have at least one diagnosis parameter 126 that matches at least one of the patient's numeric analyte values. As shown in block 270, once the rules 124 have been gathered, the system then sorts through and suppresses all of the rules found and saved during the previous step 260 whose entire set of diagnosis parameters 126 are duplicated in another rule, or that make up a subset of another rule 124. Finally, as shown in block 290, a report is generated using the selected rules 124 from the previous step 270 and displayed on an output device 140 (FIG. 1).

The method of the present invention involves the collection of patient information including test results, pharmaceutical use information, present physical conditions and past physical conditions, as well as other data either provided by the patient or collected in other ways. The information obtained from the patient may include pharmaceutical use information such as: medication currently taken, medication taken in the past and the side effects occuring as a result of medication taken. Furthermore, the patient provides a medical history, vitals information and other presently occurring symptoms. The treating professional may also enter patient complaints. The treating professional may then order certain tests based on the information provided by the patient or the treating professional may follow a regular course of diagnosis.

The present invention can be adapted for use with blood, hair, urine, saliva, and stool test results, among others. Each test will give rise to at least one test result or analyte. For example, a hair test might provide the following analytes: lead level, mercury level and/or arsenic level. The analytes can then be converted into numeric analyte values during the rating process 300. Any other medical test can be used with the present invention provided the test results can be converted into numeric analyte values. Once the test results and patient information is entered into the system, the treating professional has the opportunity to select which tests will contribute to the diagnosis.

Figure 3:
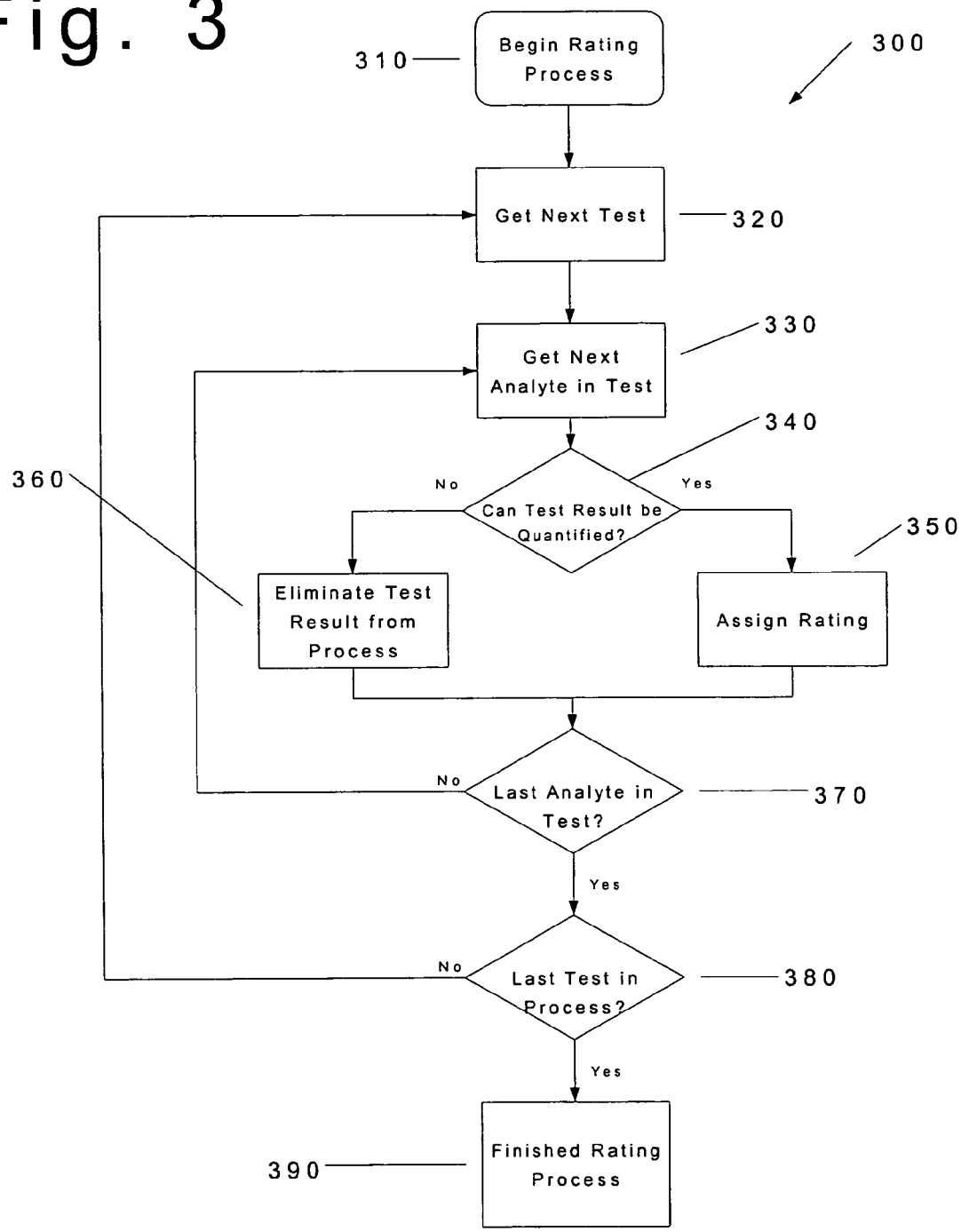
FIG. 3 is a flow chart illustrating the rating process of the method of FIG. 2.

Referring now to FIG. 3, once the test results have been entered into the computerized system 100 (see FIG. 1) using input device 130, the system begins to rate each of the analytes. As shown in blocks 310 and 320, the rating process 300 begins with the selection of the first test to analyze. Each test may have several analytes within that test and each is taken in turn, as shown in block 330. The first analyte of the first test is addressed as follows. If the analyte can be quantified, as shown in block 340, it is converted into a numeric analyte value, as shown in block 350. If the analyte cannot be quantified, it is eliminated from the rating process, as shown in block 360, and the user is informed that the analyte will not be used for diagnosis. The next analyte within the test is then rated. As shown in block 370, this process is repeated for all analytes. Once all analytes within a specific test have been rated, another test is selected for the rating process, as shown in block 320. The rating process is repeated until every analyte within every test has been rated, as shown in block 380. At that point, the rating process is complete, as shown in block 390.

The rating process 300 is accomplished using the conversion table 121, shown in FIG. 1. The conversion table 121 is created using live patient data or any other similar data and takes unmodified medical test results and assigns the test results numeric analyte values. The conversion table 121 may be a lookup table where a specific test result is listed and assigned a corresponding numeric analyte value. For example, a patient's blood test in which the analyte glucose is between 84 and 100 mg/dL may be assigned a value of 0.

Figure 4:
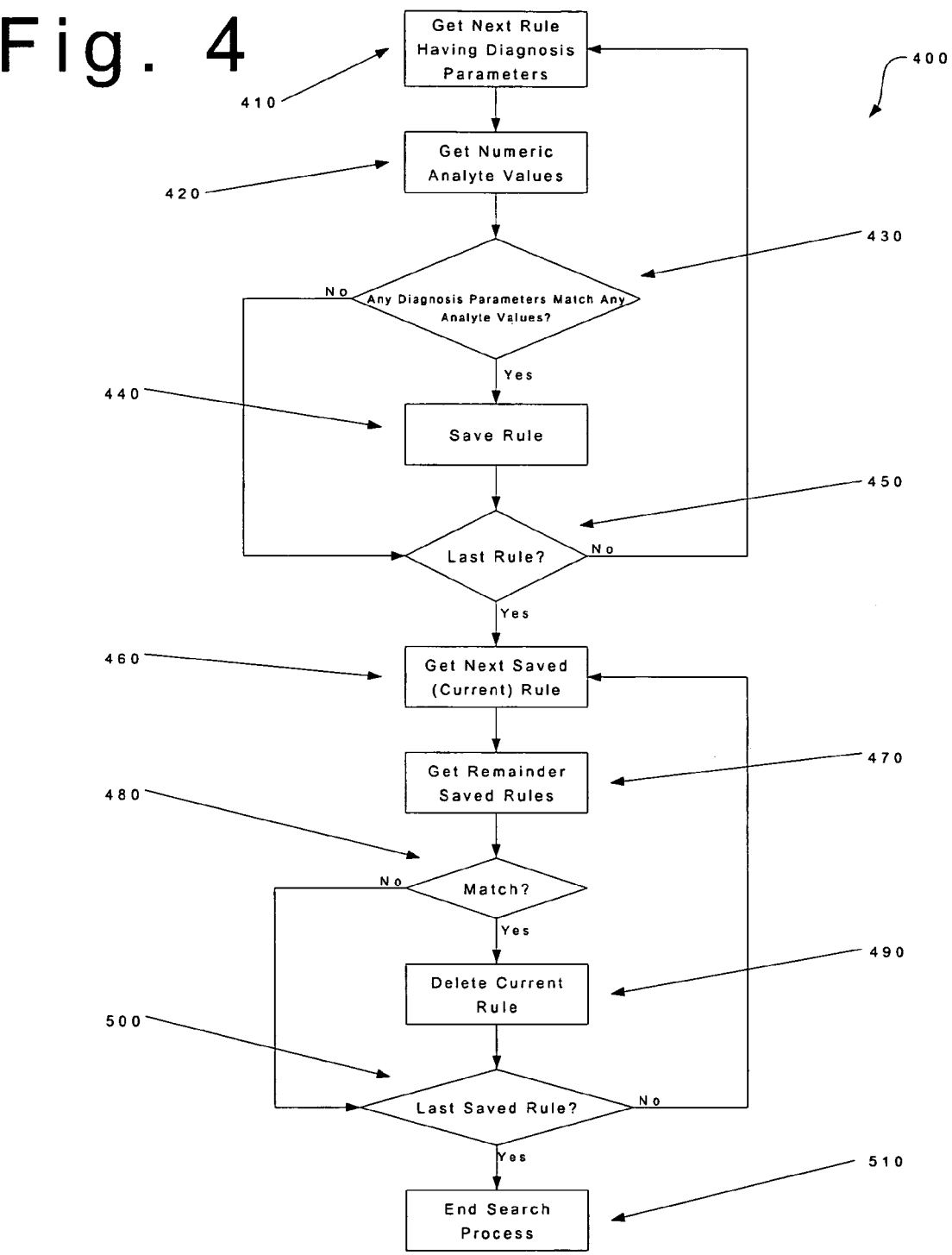
FIG. 4 is a flow chart illustrating the search process of the method of FIG. 2.

In a second embodiment of the present invention, the conversion table 121 assigns each analyte an integer value between −3 and +3; that is, a given analyte is assigned an integer value of either −3, −2, −1, 0, +1, +2 or +3. A value of −3 may correspond to critical or extremely low, −2 may correspond to clinically low, −1 may correspond to sub-healthy low, 0 may correspond to optimal, +1 may correspond to sub-healthy high, +2 may correspond to clinically high, +3 may correspond to critical or extremely high. For example, a patient's blood test in which the analyte calcium is 9.7 mg/dL may be assigned a value of −1, or sub-healthy. If an analyte cannot be assigned such a value, the analyte rating process 300 eliminates that analyte from the diagnosis process and moves to the next analyte in the test. Once each analyte of each test has been assigned a value (i.e., rated), the process moves on to the analysis portion of the present invention as shown in FIG. 4. Once the rating process 300 has rated each analyte, a series of numeric analyte values is then ready for analysis.

As stated previously and shown in FIG. 1, each of the rules 124 in the sub-diagnosis database 122 has corresponding diagnosis parameters 126 that can be compared to the numeric analyte values generated from the rating process 300. Each rule 124 consists of specific test result ranges, written text explanations of the significance of the correlated analytes, current accepted nutrition protocols including vitamin and dietary modifications, supporting text, and other related information.

Referring now to blocks 260 and 270 of FIG. 2, and more specifically to FIG. 4, the search process 400 begins at block 410 wherein the program processor begins searching each rule 124 in the sub-diagnosis database 122 for those rules having at least one diagnosis parameter 126 that matches any numeric analyte value of the specific patient. As shown in block 410, the search process begins when the system selects a first rule 124 from the sub-diagnosis database 122. Next, as shown in block 420, the system takes the numeric analyte values from the rating process 300 and compares them to the diagnosis parameters 126 of that selected first rule 124. As shown in block 430, the system then determines whether any of the diagnosis parameters 126 of that selected first rule matches any of the numeric analyte values. If there is a match, the selected first rule is designated as a target rule and therefore is saved in storage media 120, as shown in block 440. The process then continues until all rules 124 have been searched, as shown in block 450. If there is no match, the process repeats until all rules 124 in the sub-diagnosis database 122 have been searched. As shown in blocks 460, 470, 480, 490, and 500, each rule that had a match (a "target rule") and was saved in the storage media 120 is then sorted to eliminate those target rules whose diagnosis parameters are duplicated in another target rule. Target rules whose entire set of diagnosis parameters are duplicated in any other target rule, or that comprise a subset of any other target rule, are suppressed. Once each target rule has been sorted the search process is complete, as shown in block 510.

An example of the aforementioned sorting process is as follows. If a patient has numeric analyte values A, B, C, D and E after various tests have been performed and the test results rated during the rating process 300, and during the search process 400, target rule 1, having diagnosis parameters A and B is uncovered, target rule 2 with parameters B, C and D, target rule 3 with parameters A and C, target rule 4 with parameters A, B, C and D and target rule 5 with parameters A, C and E are identified, during the second portion of the search process 400, target rule 1 will be suppressed because parameters A and B are found in target rule 4. Target rule 2 also will be suppressed because parameters B, C and D are found in target rule 4. Target rule 3 will be suppressed as well because parameters A and C are found in target rule 4. However, target rule 5 will be saved because, although parameters A and C are found in target rule 4, parameter E is unique to target rule 5. Therefore, in this example target rules 4 and 5 are saved while target rules 1, 2 and 3 are suppressed.

The target rules remaining after the search process 400 form the diagnosis. A final diagnosis may have several rules 124 based on several analytes and their correlations. The rules 124 that have been suppressed are not included in the final diagnosis. Once the list of rules 124 has been generated, it can be printed out in report form using output device 140 or stored in electronic format.

A third embodiment of the present invention adds an additional and more descriptive diagnosis. The third embodiment utilizes a diagnosis database 128 that is stored on the storage media 120 of the computerized system 100 (see FIG. 1). The diagnosis database 128 consists of many detailed diagnoses 131, each corresponding to a specific rule 124. The search process 400 retrieves each rule 124 as discussed above, then matches a detailed diagnosis 131 to that rule 124. Duplicate detailed diagnoses 131 are then excluded. The final detailed diagnosis includes the rules 124 as generated above and the corresponding detailed diagnoses 131.

A fourth embodiment of the present invention includes storing a supporting findings database 129 in the storage media 120 of the computerized system 100 (see FIG. 1). The supporting findings database 129 includes a list of supporting findings 132 that correspond to the detailed diagnoses 131 discussed above. Once a detailed diagnosis 131 has been matched to a specific rule 124 and duplicate detailed diagnoses 131 excluded, a list of supporting findings 132 that correspond to each of the detailed diagnoses 131 is generated and may be listed in the detailed report. The supporting findings 132 may be other test findings and may include several different analytes that directly contribute to the detailed diagnosis 131. These individual analytes are rated high or low for each specific diagnosis. When a detailed diagnosis 131 is given, all of the related supporting findings 132 are saved and listed with that detailed diagnosis. For example, a patient may have a detailed diagnosis 131 of anemia. Other test results that support this include blood in the stool and urine, high levels of lead, arsenic, and mercury, high SGOT and SGPT, and low serum iron and ferritin. Therefore, these are the supporting findings. There are many other possible analytes that may support anemia, however, in this example only those listed were specific to the patient and support the finding of anemia.

Figure 5:
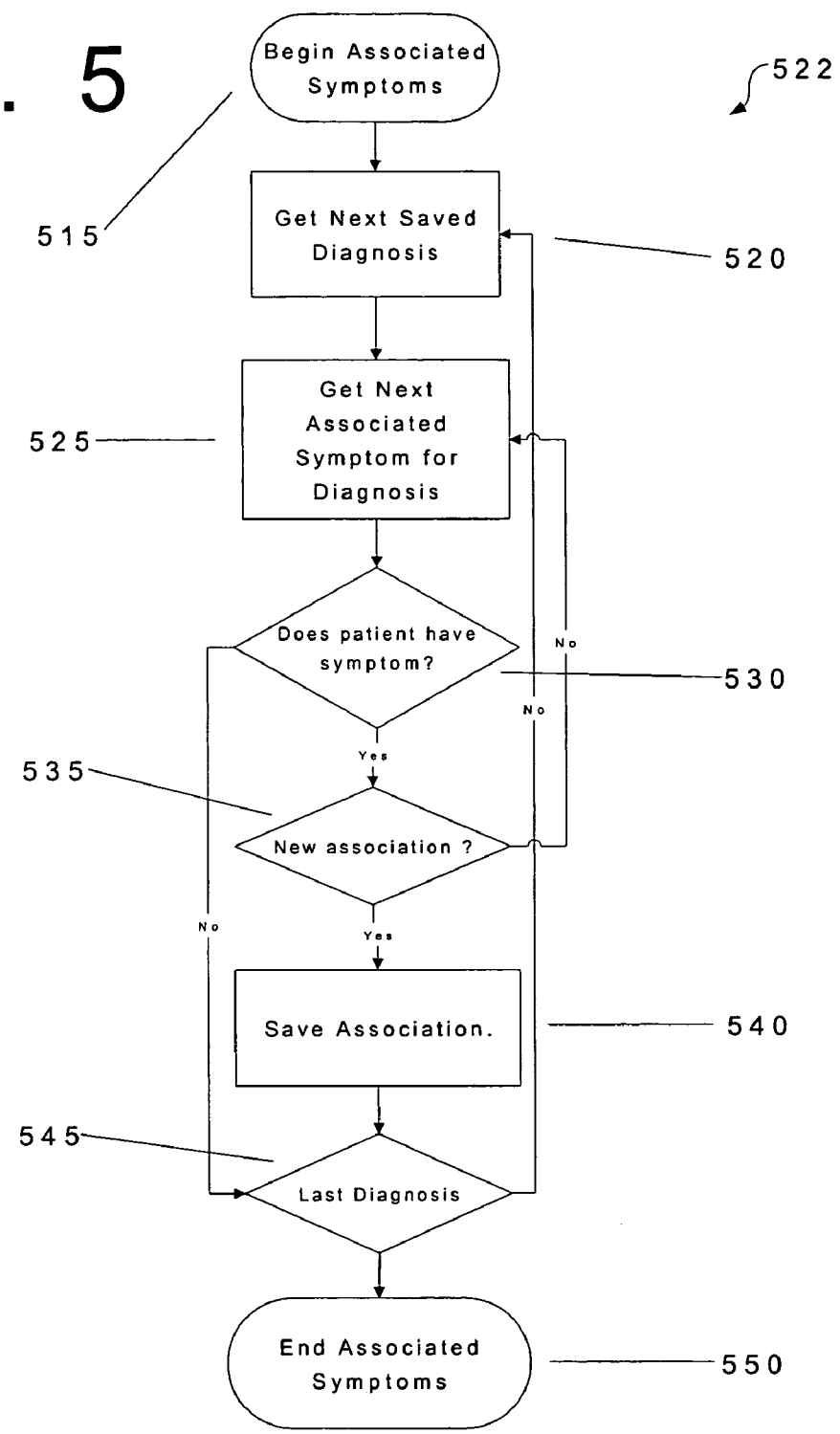
FIG. 5 is a flow chart illustrating the process for generating a list of associated symptoms of the method of FIG. 2.

In a fifth embodiment of the present invention, a list of associated symptoms may be generated. An associated symptom is a symptom reported by the patient during an interview, or provided on a patient symptom survey, that is associated with a specific detailed diagnosis 131. As shown in blocks 515 and 520 of FIG. 5, the process 522 for generating a list of associated symptoms begins with the selection of the first detailed diagnosis 131 that was obtained in the processes discussed in detail above. As shown in block 525, each diagnosis 131 may include a list of symptoms associated therewith. The list may be stored in the storage media 120 of the computerized system 100. Each symptom associated with the diagnosis 131 is compared to the list of symptoms provided by the patient, as shown in block 530. As shown in blocks 535 and 540, if there is a matching symptom, the symptom is saved. The process is repeated until each symptom of each diagnosis 131 generated for the patient has been compared to the patient's symptoms, as shown in blocks 545 and 550. The list of associated symptoms may then be saved and/or printed in the detailed report. For example, a patient may have a detailed diagnosis of anemia. The symptoms associated with anemia include fatigue, poor concentration, cold hands, and cold feet, among many others. However, the patient may only report fatigue and cold hands in the patient symptom survey. Therefore, the list of associated symptoms in the detailed report will include fatigue and cold hands.

Figure 6:
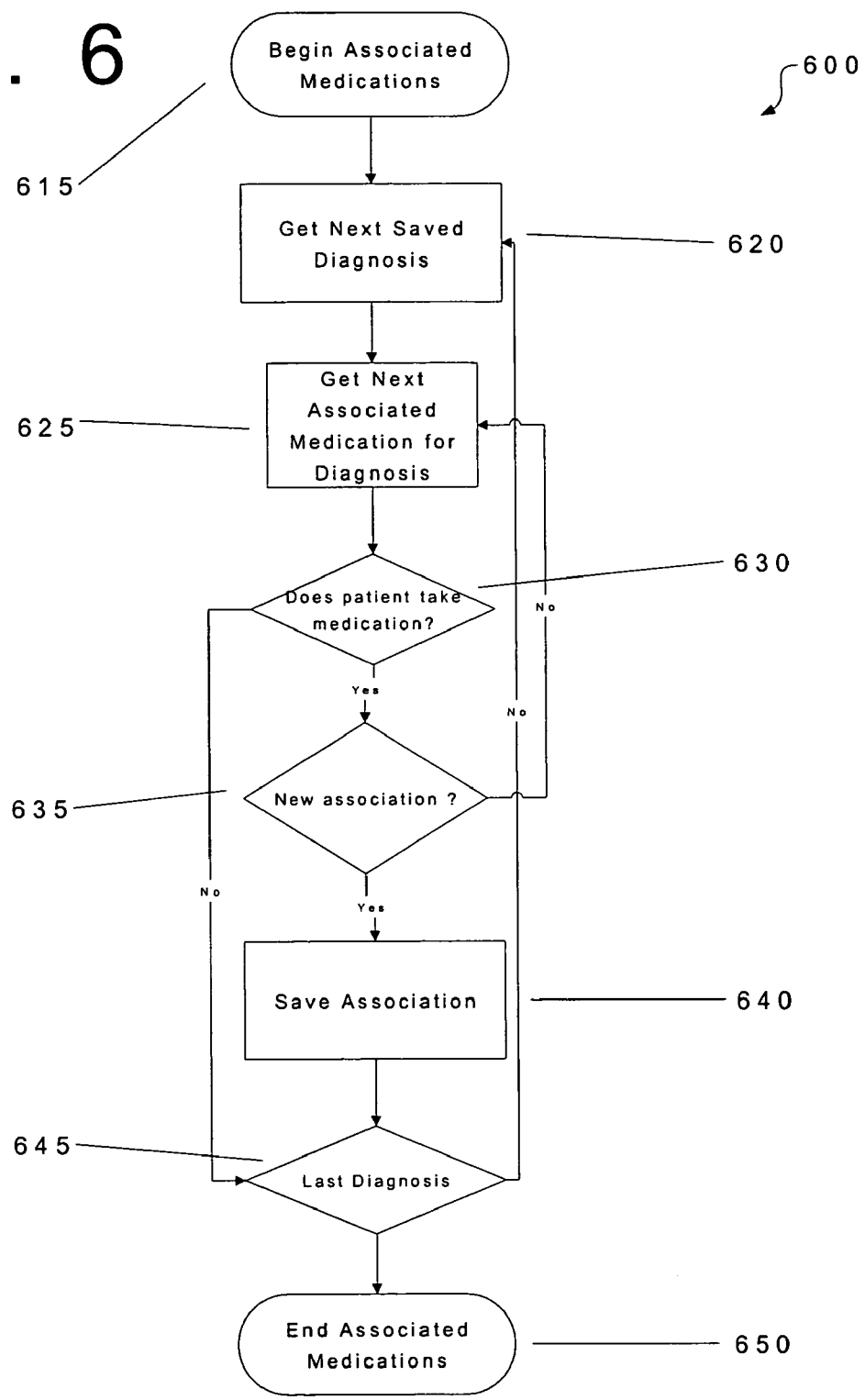
FIG. 6 is a flow chart illustrating the process for generating a list of associated medications of the method of FIG. 2.

In a sixth embodiment of the present invention a list of associated medications may be generated. An associated medication is a medication used by the patient and reported during an interview, or provided on a patient symptom survey, that is associated with a specific detailed diagnosis 131 because it directly or indirectly causes or contributes to the diagnosis. As shown in blocks 615 and 620 of FIG. 6, the process 600 for generating a list of associated medications begins with the selection of the first detailed diagnosis 131, as obtained in the processes discussed in detail above. Each diagnosis 131 may include a list of medications that may be associated therewith, and the list may be stored in the storage media 120 of the computerized system 100, as shown in block 625. Each medication associated with the diagnosis 131 is compared to the list of medications provided by the patient, as shown in block 630. As shown in blocks 635 and 640, if there is a matching medication, the medication is saved. The process is repeated until each medication associated with each diagnosis 131 generated for the patient has been compared to the patients medications, as shown in blocks 645 and 650. The list of associated medications may then be saved and/or printed in the detailed report. For example, a patient may have a detailed diagnosis of anemia. The medications associated with anemia include Naprosyn, Zoloft, Micronase, and Prilosec, among many others. However, the patient may only report taking Zoloft and Prilosec in the patient symptom survey. Therefore, the list of associated medications in the detailed report will include Zoloft and Prilosec.

Figure 7:
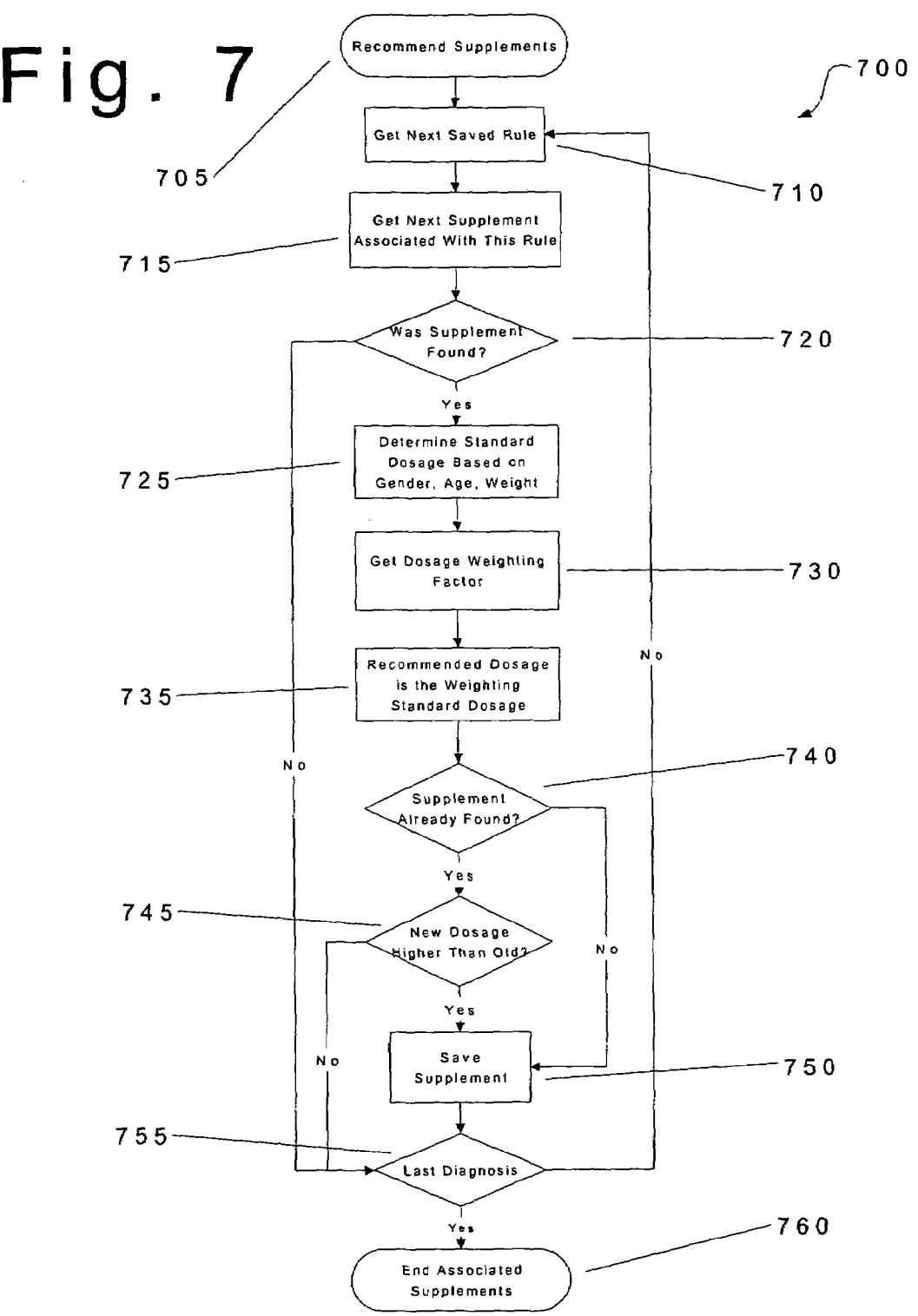
FIG. 7 is a flow chart illustrating the process for generating a list of recommended supplements of the method of FIG. 2.

In a seventh embodiment of the present invention a list of recommended supplements may be generated. As shown in blocks 705 and 710 of FIG. 7, the process 700 for generating a list of recommended supplements begins with the selection of the first rule 124 saved for that patient. Each rule 124 may include a list of supplements that may be beneficial for that rule and the list may be stored in the storage media 120 of the computerized system 100. The dosage for each individual supplement is determined one at a time, as shown in blocks 715 and 720. As shown in block 725, a standard dosage is first determined based on the patient's weight, sex and age. The standard dosage of a nutrient is not related to any given rule. Instead, it is only specific to the given nutrient. This allows for multiple suppliers of vitamin supplements to have only their specific nutrients listed with each rule and the final list of supplements. As shown in blocks 730 and 735, the standard dosage is weighted to obtain the recommended dosage. The weighting of each dosage is dependant on the rating of the analytes in the rule 124, as obtained in the rating process 300. For example, a mild anemia may be assigned a weighting factor of +1 for the vitamin B12 supplement that may correspond to 1 gram of vitamin B12 per day. Alternatively, extreme anemia may be assigned a weighting factor of +2 for the vitamin B12 supplement that may correspond to 2 grams of vitamin B12 per day. As shown in blocks 740, 745, 750, and 755, the process is repeated such that each supplement of each rule is considered and a recommended dosage is obtained without duplicating dosages. If more than one rule 124 recommends the same supplement, only the highest recommended dosage is retained and reported to the patient. As shown in block 760, the process 700 is complete when a list of recommended supplements is generated giving recommended dosages specific to a patient's condition.

In an eighth embodiment of the present invention the report generated according to the method described above further includes a colored blood results chart. The colored blood results chart sets forth the results of a patient's blood test and indicates the severity of each test result or analyte with a designated color.

For example, a patient's blood may be tested for the following analytes: glucose, creatinine, ferritin and LDL cholesterol. The following laboratory test results may be obtained: glucose measures at 95 mg/dL, creatinine measures at 0.92 mg/dL, ferritin measures at 26 ng/dL and LDL cholesterol measures at 111 mg/dL. The method of the present invention, as described above, may rate each of these test results as follows: glucose may be optimal and receive a rating of 0, creatinine may be sub-healthy high and receive a rating of +1, ferritin may be clinically low and receive a rating of −2 and LDL cholesterol may be extremely high and receive a rating of +3.

Each of the test results may be listed in the report and highlighted with a color that corresponds to the numeric rating as obtained above. The color blue means crisis and corresponds to −3 extremely low or +3 extremely high. The color red means danger and corresponds to −2 clinically low or +2 clinically high. The color yellow means warning and corresponds to −1 sub-healthy low or +1 sub-healthy high.

Referring to the example above, the report may list the analytes tested, the laboratory results obtained, and, depending on the rating of each test result, the results may be highlighted a specific color corresponding to the severity of the condition. Therefore, the result for glucose will not be highlighted because it is at an optimal level. However, creatinine may be highlighted yellow, ferritin may be highlighted red and LDL cholesterol may be highlighted blue.

Further, the present invention may compare two blood tests side by side to determine progress and report the progress using various indicia. The user or medical professional may select which test to compare with the most recent or current test. For example, a patient may have had 9 blood tests performed in the past, and each analyzed and saved according to the present invention. The results of past blood test may then be compared to the present blood test results. The immediately previous results may be defaulted for comparison, however, the user or medical professional may select any one of the previous blood tests for comparison.

A delta of a green smiley face may be used to indicate progress with respect to a specific blood test when comparing the most recent test result with the previous test. A specific blood test may be highlighted in red and at the same time have a green smiley face that indicates that the test result has improved. A delta of a red frowning face may be used to indicate that a specific blood test is worse comparing the most recent test with the previous test selected. A delta of a yellow straight face indicates that the test result has remained unchanged.

There are many benefits and advantages to using a colored blood results chart, including the ability to easily and quickly assess the results of treatment and avoid the problems associated of flipping through charts trying to find the proper charts and identifying the problematic test results. Further, an advantage of this feature is that a comprehensive test may have been done when the patient first presented. If a patient had an extreme infection or very high glucose, a test may be done quickly to determine if progress in these critical values is improving. Three of these small specific tests may have been done within a couple of weeks. Then, two months after the patient was first tested, another comprehensive test may be done to get a more complete picture of the status of the blood. The user or medical professional may enter the most recent blood test and the very first test could be selected to compare the results. Thereby, the patient's progress may be determined as compared to the initial testing. A still further advantage is that the present invention may list 7 blood tests. Two of which may be for comparison and the remaining five may be based on recent chronology. This will help the doctor and patient chart their progress over an extended period. All of these charts will be listed with the blue, red and yellow color rating.

The present invention uses data comprised of accepted medical nutritional research. The invention takes data indicative of a patient's present symptoms and enters it into a computerized system 100 of the present invention. The information then correlated with other data, such as the patient's vitals, medications, blood tests, hair tests, urinalysis, occult stool analysis, saliva and urinary tests as well as many other tests. As is apparent from the above description, the more testing that is done on a patient, the more comprehensive the report for that patient will be. The present invention is designed to be able to add any test whose results may be quantified. This invention takes all parameters and correlates them, building a comprehensive computer analysis report specific to a patient. The present invention allows a treating professional to add comments and exam findings directly into the report, as shown in block 280 of FIG. 2. Patient comments may also be included (see block 280). The report may also include a color chart of results that easily identifies the status of each analyte. The report may also note dietary modifications and specific vitamins and dosages based on a patient's age, sex, weight and severity of condition. All of the above mentioned parameters, tests and variables contribute to a report that is specific to each patient. An advantage of the report of the present invention is that the report generated is so comprehensive that the treating professional may not have to review it with the patient since the patient gets a thorough report that may be taken home and reviewed repeatedly. A minimally trained staff is sufficient to perform the method of the present invention.

Although the invention is shown and described with respect to certain embodiments, it is obvious that equivalents and modifications will occur to others skilled in the art upon reading and understanding the specification. The present invention includes all such equivalents and modifications and is limited only by the scope of the claims.

What is claimed is:

1. A method for generating a medical diagnosis comprising the steps of:
   creating a conversion table and storing said table in a computerized storage media of a computerized system, wherein said conversion table converts medical test data into numeric analyte values;
   creating a sub-diagnosis database and storing said sub-diagnosis database in said storage media, said sub-diagnosis database including a plurality of rules, each rule of said plurality of rules being identified by at least one diagnosis parameter;
   inputting at least one test result of a patient in said computerized system;
   converting said test result to at least two numeric analyte values by said conversion table;
   searching said rules in said sub-diagnosis database for at least one target rule having at least one of said diagnosis parameters corresponding to at least one of said numeric analyte values;
   saving said target rules identified in said searching step, wherein said saving step includes the step of excluding those of said target rules whose entire diagnosis parameters are duplicated in, or comprise a subset of, another single target rule; and
   generating a report listing at least one of said target rules found in said searching step.

2. The method of claim 1, further comprising the steps of:
   storing a diagnosis database in said computerized system, said diagnosis database including a plurality of diagnoses, each of said diagnoses corresponding to a particular one of said target rules; and
   generating a detailed report using said target rules coupled with said corresponding diagnoses.

3. The method of claim 1, wherein said sub-diagnosis database is populated with data obtained from live patient examinations.

4. The method of claim 1, further comprising the step of inputting survey data of a patient in said computerized system, said survey data being converted to at least one numeric analyte value by said conversion table.

5. The method of claim 1, further comprising the step of inputting pharmaceutical use data of a patient in said computerized system, said pharmaceutical use data being converted to at least one numeric analyte value by said conversion table.

6. The method of claim 2, further comprising excluding each duplicate one of the plurality of diagnoses in said detailed report.

7. The method of claim 6, wherein said detailed report further includes vitamin and supplement recommendations.

8. The method of claim 6, wherein said detailed report further includes a list of associated symptoms.

9. The method of claim 6, wherein said detailed report further includes a list of associated medications.

10. The method of claim 6, wherein said detailed report further incudes a colored blood results chart.

11. The method of claim 6, wherein said detailed report further includes supporting findings.

12. A method for generating a medical diagnosis comprising the steps of:
    creating a conversion table and storing said table in a computerized storage media of a computerized system, wherein said conversion table converts medical test data into numeric analyte values;
    creating a sub-diagnosis database and storing said sub-diagnosis database in said storage media, said sub-diagnosis database including a plurality of rules, each rule of said plurality of rules being identified by at least one diagnosis parameter;
    inputting at least two test results of a patient in said computerized system;
    converting each of said test results to at least one numeric analyte value by said conversion table;
    searching said rules in said sub-diagnosis database for at least one target rule having at least one of said diagnosis parameters corresponding to at least one of said numeric analyte values;
    saving said target rules identified in said searching step, wherein said saving step includes the step of excluding those of said target rules whose entire diagnosis parameters are duplicated in, or comprise a subset of, another single target rule; and
    generating a report listing at least one of said target rules found in said searching step.

13. The method of claim 12, further comprising the steps of:
    creating a diagnosis database and storing said diagnosis database in said storage media, said diagnosis database including a plurality of diagnoses, each of said diagnoses corresponding to a particular one of said target rules; and
    generating a detailed report using said target rules coupled with said corresponding diagnoses.

14. The method of claim 12, wherein said sub-diagnosis database is populated with data obtained from live patient examinations.

15. The method of claim 12, further comprising the steps of inputting survey data of a patient in said computerized system, said survey data being converted to at least one numeric analyte value by said conversion table.

16. The method of claim 12, further comprising the step of inputting pharmaceutical use data of a patient in said computerized system, said pharmaceutical use data being converted to at least one numeric analyte value by said conversion table.

17. The method of claim 13, further comprising excluding each duplicate one of said plurality of diagnoses in the detailed report.

18. The method of claim 17, wherein said detailed report further includes vitamin and supplement recommendations.

19. The method of claim 17, wherein said detailed report further includes a list of associated symptoms.

20. The method of claim 17, wherein said detailed report further includes a list of associated medications.

21. The method of claim 17, wherein said detailed report further includes a colored blood results chart.

22. The method of claim 17, wherein said detailed report further includes supporting findings.

23. A system for medical diagnosis comprising:
- a computerized system having a computerized storage media and a computerized processor;
- an input device workably interconnected with said computerized system to allow a user to input test results to said computerized system;
- a conversion table stored in said storage media for converting at least one test result input by said user into at least two numeric analyte values; and
- a sub-diagnosis database stored in said storage media, said sub-diagnosis database including a plurality of rules, each rule of said plurality of rules being identified by at least one diagnosis parameter, wherein said system searches said rules in said sub-diagnosis database and saves at least one target rule having at least one of said diagnosis parameters corresponding to at least one of said analyte values,
- wherein said system generates a report listing at least one said target rule saved by said system and wherein said system excludes those of said target rules whose entire diagnosis parameters are duplicated in, or comprise a subset of, another single target-rule.

24. The system of claim 23, further comprising a diagnosis database stored in said storage media, said diagnosis database including a plurality of diagnoses, each of said diagnoses corresponding to a particular one of said target rules.

25. The system of claim 24, wherein said system generates a detailed report listing at least one of said diagnoses.

26. A system for medical diagnosis comprising:
- a computerized system having a computerized storage media and a computerized processor;
- an input device workably interconnected with said computerized system to allow a user to input test results to said computerized system;
- a conversion table stored in said storage media for converting at least two test results input by said user into at least one numeric analyte value per test result; and
- a sub-diagnosis database stored in said storage media, said sub-diagnosis database including a plurality of rules, each rule of said plurality of rules being identified by at least one diagnosis parameter, wherein said system searches said rules in said sub-diagnosis database and saves at least one target rule having at least one of said diagnosis parameters corresponding to at least one of said analyte values,
- wherein said system generates a report listing at least one said target rule saved by said system and wherein said system excludes those of said target rules whose diagnosis parameters are duplicated in, or comprise a subset of, another single target rule.

27. The system of claim 26, further comprising a diagnosis database stored in said storage media, said diagnosis database including a plurality of diagnoses, each of said diagnoses corresponding to a particular one of said target rules.

28. The system of claim 27, wherein said processor generates a detailed report listing at least one of said diagnoses.

* * * * *